United States Patent [19]

Stout et al.

[11] Patent Number: 4,778,807

[45] Date of Patent: Oct. 18, 1988

[54] SUBSTITUTED 2-AMINO-2-IMIDAZOLINES AS ANTIFIBRILLATORY AGENTS

[75] Inventors: David M. Stout; William L. Matier, both of Libertyville; Lawrence A. Black, Vernon Hills, all of Ill.

[73] Assignee: E. I. Du Pont de Nemours & Company, Wilmington, Del.

[21] Appl. No.: 106,662

[22] Filed: Oct. 13, 1987

[51] Int. Cl.$^4$ .................. A61K 31/415; A61K 31/40; C07D 233/48; C07D 413/04

[52] U.S. Cl. .............................. 514/401; 514/235.8; 514/326; 514/402; 546/210; 544/139; 548/348; 548/351

[58] Field of Search ............... 548/348, 351; 514/401, 514/402

[56] References Cited

U.S. PATENT DOCUMENTS 4,661,602 4/1987 Myers et al. .................. 548/348

Primary Examiner—Mary C. Lee
Assistant Examiner—J. Richter

Attorney, Agent, or Firm—Gildo E. Fato

[57] ABSTRACT

Described are compounds of the formula:

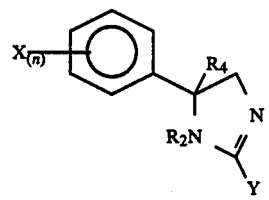

wherein Y denotes dimethylamino, methylpropynylamino, pyrrolidino, piperidino, or morpholino; $R_1$ and $R_2$ independently of each other denote hydrogen or loweralkyl; and X denotes loweralkyl, loweralkoxy, or halo; and n is and integer from 1 to 3 inclusive, or pharmaceutically acceptable salts thereof.

The compounds exhibit antiarrhythmic activity without unwanted sympathomimetic effects.

21 Claims, No Drawings

SUBSTITUTED 2-AMINO-2-IMIDAZOLINES AS ANTIFIBRILLATORY AGENTS

BACKGROUND OF THE INVENTION

Irregularity in the rhythm of the heart may result from several possible underlying causes which may be hormonal, metabolic (electrolyte imbalance) or circulatory (blood loss, faulty heart valve) in nature. In addition, substances such as tobacco, caffeine, or digitalis may also cause cardiac rhythm disturbances.

One type of cardiac rhythm irregularity is fibrillation, a pathological condition of heart muscle which may be present in either the atria or the ventricles. Atrial fibrillation is an atrial arrhythmia characterized by rapid randomized contractions of the atrial myocardium, causing a totally irregular, often rapid ventricular rate. Ventricular fibrillation is an arrhythmia characterized by fibrillary contractions of the ventricular muscle due to rapid repetitive excitation of the myocardial fibers without coordinated contraction of the ventricles. These arrhythmias can be eliminated by the use of electric shock or through the use of certain antiarrhythmic agents. However, although fibrillation can be converted to normal sinus rhythm by the use of antifibrillatory agents, prevention of its recurrence requires chronic therapy for long periods of time. Consequently, these antifibrillatory drugs must not only be effective but they should possess minimal adverse side-effects.

The prevention of sudden coronary death has become a major focus of cardiovascular therapy. The primary cause of sudden coronary death is ventricular fibrillation. Unfortunately, none of the currently available antiarrhythmic drugs is considered suitable for long-term prophylactic use in the prevention of sudden coronary death, nor are any of the newer agents currently under investigation known to prevent ventricular fibrillation. The only currently marketed drug having the potential for the suppression of recurrent ventricular tachyarrhythmias and recurrent ventricular fibrillation is bretylium tosylate; however, it is only used in the acute care setting, primarily due to the possible occurrence of unwanted side effects. These side effects consist of an initial sympathomimetic effect characterized by a significant increase in both heart rate and blood pressure, followed by an antiadrenergic effect which is manifested by the patient becoming dizzy if in a position other than supine. In addition, due to its poor oral bioavailability, bretylium tosylate is only administered intravenously. An experimental antifibrillatory drug, bethanidine, is orally active but it too possesses the unwanted side effects of bretylium. Thus, a great need exists for an orally active drug that will prevent life-threatening ventricular dysrhythmias without the serious side effects of tachycardia and hypertension associated with bretylium tosylate and bethanidine.

In accordance with the present invention, disclosed are compounds having effective antiarrhythmic activity with less of the unwanted activity related to the use of these anti-arrhythmic drugs.

SUMMARY OF THE INVENTION

The present invention is directed to compounds of the formula:

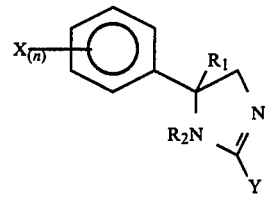

wherein Y denotes dimethylamino, methylpropynylamino, pyrrolidino, piperidino, or morpholino; $R_1$ and $R_2$ independently of one another denote hydrogen or loweralkyl; X denotes loweralkyl, loweralkoxy, or halo; and n is an integer from 1 to 3 inclusive, or pharmaceutically accepted salts thereof.

The terms "loweralkyl" and "loweralkoxy" as used herein refer to straight or branched chain alkyl radicals containing from 1 to 6 carbon atoms including but not limited to methyl, ethyl, n-propyl, iso-propyl, n-butyl, t-butyl, n-pentyl, 1-methylbutyl, 2,2-dimethylbutyl, 2-methylpentyl, 2,2-dimethylpropyl, n-hexyl and the like.

The term "halo" as used herein refers to chloro, bromo, fluoro and iodo.

The term "pharmaceutically acceptable salts" includes nontoxic acid addition salts of the compounds of the invention which are generally prepared by reacting the free base with a suitable organic or inorganic acid. Representative salts include the hydrochloride, hydrobromide, hydroiodide, sulfate, bisulfate, acetate, oxalate, valerate, oleate, palamitate, stearate, laurate, borate, benzoate, lactate, phosphate, tosylate, citrate, maleate, fumarate, succinate, tartrate, and like salts.

The present compounds may be administered to warm-blooded animals orally or parenterally. They can generally be administered with a pharmaceutical carrier. The term "pharmaceutical carrier", for the purpose of the present invention, is intended to refer to any medium that is suitable for the preparation of a dosage unit form, and, thus, includes the tablet medium or a pharmaceutically acceptable vehicle or solvent such as is ordinarily used in the preparation of intravenous or intramuscular solutions.

A pharmaceutical composition containing the compound can be administered to warm-blooded animals in topical, parenteral or oral dosage form. For oral administration, amounts of from about 0.14 to 71 mg/kg per day per patient are useful, with the total dose of up to 0.01 to 5.0 grams per day being a suitable range for large animals, including humans. A preferred dosage range is from about 0.01 to 1.0 grams total daily dosage in a single or divided dose.

For all dosage forms, the above exemplified compounds can be placed in capsules, formulated into pills, wafers, or tablets in conventional fashion together with pharmaceutical carriers well known in the art. Tablets may be prepared for immediate release of the active compound or they may be made enteric, i.e., whereby the active ingredient is released slowly over a period of several hours from within the intestinal tract.

DETAILED DESCRIPTION OF THE INVENTION

The compounds of the present invention can be prepared most advantageously by one of several methods as hereinafter described, depending on the final product desired.

In order to illustrate the manner in which the above compounds may be prepared and the properties of the compounds, reference is made to the following examples which, however, are not meant to limit or restrict the scope of the invention in any respect. Various physical constants of the compounds presented appear in Table I.

The compounds of the present invention and equivalents thereof possessing substantially similar pharmacological properties may be prepared from the appropriate diamines or 2-methylthioimidazolines by one of the three methods described below. Preparation of the prerequisite diamines and 2-methylthioimidazolines as well as their alpha-aminonitrile precursors is described in the following publications: Matier, W. L.; Owens, D. A.; Comer, W. T.; *J. Med. Chem.*, 1973, 16, 901; Stout, D. M.; Black, L. A.; Matier, W. L.; *J. Org. Chem.*, 1983, 48, 5369; Mai, K. and Patil, G.; *Tet. Lett.*, 1984, 25, 4583.

METHODS OF PREPARATION

A. Primary 2-aminoimidazolines (Y=NH$_2$, Table II) were prepared by reacting cyanogen bromide with diamines obtained through literature procedures. As an example, a solution of beta-amino-4-methoxyphenethylamine (4.5 g, 0.0275 mole) in 70 mL toluene was treated with a solution of cyanogen bromide (2.9 g, 0.0275 mole) in 35 mL to give a white precipitate. This reaction mixture was stirred at room temperature for four hours, then the precipitate was collected by filtration. Crystallization of the precipitate from ethanol afforded 4.7 g (62.8% yield) of compound 2.

B. Secondary and tertiary 2-aminoimidazolines in which R$_2$=H (Table II) were prepared by reacting the appropriate amine with the 2-methylthioimidazoline obtained through literature procedures. As an example, a solution of 2-methylthio-4-(4'-methoxyphenyl)-2-imidazoline hydroiodide (6.0 g, 0.0171 mole) and 40% aq. dimethylamine (3.86 g, 0.0342 mole) in 30 mL methanol and 30 mL water was stirred at reflux for 16 hours. Volatile materials were removed under reduced pressure to give a solid. This solid was crystallized from methanol/diethylether to afford 3.2 g (53.9% yield) of compound 6.

C. Secondary and tertiary 2-aminoimidazolines in which R$_2$ is a group other than hydrogen were prepared by vigorously reacting the desired amine with the appropriately substituted 2-methylthioimidazoline obtained through literature procedures. As an example, a solution of 2-methylthio-3-methyl-4-(4'-methoxyphenyl)-2-imidazoline hydroiodide (8.0 g, 0.022 mole) and 40% aq. methylamine 17.0 mL, 0.197 mole) in 100 mL of methanol was sealed in a stainless steel reaction bomb and heated to 110° C. for 6 hours. Volatile materials were then removed under reduced pressure to give a white solid. This material was crystallized from methanol/diethylether to afford 5.6 g (73.3% yield) of white crystalline compound 10.

TABLE I

| Compound | Preparation (Reaction Solvent) | Crystallization Solvent | MP (°C.) | H NMR (δ) | [α]$_D$ |
|---|---|---|---|---|---|
| 1 | B(CH$_3$OH/H$_2$O) | CH$_3$CH$_2$OH/(CH$_3$CH$_2$)$_2$O | 169-170 | [CD$_3$OD] 2.93s (6H), 3.50dd (1H, J=8Hz, 10Hz), 4.17t (1H, J=10Hz), 5.20dd (1H, J=8Hz, 10Hz), 7.20-7.67m (3H) | — |
| 2 | A (toluene) | CH$_3$CH$_2$OH | 208-209 | [D$_2$O/CD$_3$OD] 3.47dd (1H, J=8Hz, 10Hz), 3.78s (3H), 4.02t (1H, J=10Hz), 5.07dd (1H, J=8Hz, 10Hz), 6.95d (2H, J=8Hz), 7.28d (2H, J=8Hz) | — |
| 3 | A (toluene) | CH$_3$CH$_2$OH | 193-194 | [D$_2$O/CD$_3$OD] 3.40t (1H, J=9Hz), 3.63s (3H), 3.90t (1H, J=9Hz), 4.58s (2H), 4.72t (1H, J=9Hz), 6.67-7.47m (9H) | — |
| 4 | A (toluene) | CH$_3$CH$_2$OH | 215-216 | [d$_6$-DMSO] 3.40dd (1H, J=8Hz, 10Hz), 4.10t (1H, J=10Hz), 5.22dd (1H, J=8Hz, 10Hz), 7.30-7.80m (3H), 7.90-8.13s (1H) | — |
| 5 | A (toluene) | CH$_3$CH$_2$OH/(CH$_3$CH$_2$)$_2$O | 150-151 | [CD$_3$OD] 3.45dd (1H, J=7Hz, 9Hz), 3.73s (3H), 4.08t(1H, J=9Hz), 5.08dd (1H, J=7Hz, 9Hz), 6.72-7.45m (3H) | — |
| 6 | B(CH$_3$OH/H$_2$O) | CH$_3$OH/(CH$_3$CH$_2$)$_2$O | 125-128 | [CD$_3$OD] 3.17s (6H), 3.57dd (1H, J=8Hz, 10Hz), 3.83s (3H), 4.17t (1H, J=10Hz), 5.25dd (1H, J=8Hz, 10Hz), 7.05d (2H, J=8Hz), 7.48d (2H, J=8Hz) | — |
| 7 | B(CH$_3$OH/H$_2$O) | CH$_3$OH/(CH$_3$CH$_2$)$_2$O | 166-167 | [CD$_3$OD] 3.07s (6H), 3.50dd (1H, J=8Hz, 10Hz), 3.77s (3H), 4.13t (1H, J=10Hz), 5.17dd (1H, J=8Hz, 10Hz), 6.97d (2H, J=8Hz), 7.40d (2H, J=8Hz) | +17.85 |
| 8 | B(CH$_3$OH/H$_2$O) | CH$_3$OH/(CH$_3$CH$_2$)$_2$O | 165-166 | [CD$_3$OD] 3.10s (6H), 3.50dd (1H, J=8Hz, 10Hz), 3.77s (3H), 4.12t (1H, J=10Hz), 5.17dd (1H, J=8Hz, 10Hz), 6.95d (2H, J=8Hz), 7.38d (2H, J=8Hz) | -17.80 |
| 9 | A (toluene) | CH$_3$OH/(CH$_3$CH$_2$)$_2$O | 312 | [d$_6$-DMSO] 2.67s (3H), 3.33dd (1H, J=8Hz, 10Hz), 3.73s (3H), 3.92t (1H, J=10Hz), 4.17s (3H), 4.87dd (1H, J=8Hz, 10Hz), 6.95d (2H, J=8Hz), 7.30d (2H, J=8Hz) | — |
| 10 | C(CH$_3$OH) | CH$_3$OH/(CH$_3$CH$_2$)$_2$O | 198-199 | [CD$_3$OD] 2.72s (3H), 3.00s (3H), 3.47dd (1H, J=8Hz, 10Hz), 3.77s (3H), 4.07t (1H, J=10Hz), 4.98dd (1H, J=8Hz, 10Hz), 6.95d (2H, J=8Hz), 7.35d (2H, J=8Hz) | — |
| 11 | C(dry CH$_3$OH) | CH$_3$OH/(CH$_3$CH$_2$)$_2$O | 135-136 | [d$_6$-DMSO] 2.92s (3H), 3.10s (6H), 3.33dd (1H, J=8Hz, 10Hz), 3.77s (3H), 4.03t (1H, J=10Hz), 4.97dd (1H, J=8Hz, 10Hz), 7.00d (2H, J=8Hz), 7.40d (2H, J=8Hz) | — |
| 12 | A (toluene) | CH$_3$OH/(CH$_3$CH$_2$)$_2$O | 218-219 | [CD$_3$OD] 2.83s (3H), 3.50dd (1H, J=8Hz, 10Hz), 3.85s (3H), 4.98dd (1H, J=8Hz, 10Hz), 6.83-7.65m (4H) | — |
| 13 | C(CH$_3$OH) | CH$_3$OH/(CH$_3$CH$_2$)$_2$O | 211-213 | [CD$_3$OD] 2.75s (3H), 2.98s (3H), 3.48dd (1H, J=8Hz, 10Hz), 3.78s (3H), 4.07t (1H, J=10Hz), 4.95dd (1H, J=8Hz, 10Hz), 6.73-7.40m (4H) | — |
| 14 | B(CH$_3$OH/H$_2$O) | CH$_3$OH/(CH$_3$CH$_2$)$_2$O | 209 | [CD$_3$OD] 3.17s (6H), 3.58dd (1H, J=8Hz, 10Hz), 3.87s (3H), 3.90s (3H), 4.13t (1H, J=10Hz), 5.18dd (1H, J=8Hz, 10Hz), 6.93-7.10m (3H) | — |
| 15 | B(CH$_3$CH$_2$OH) | CH$_3$COCH$_3$/(CH$_3$CH$_2$)$_2$O | 180-182 | [CD$_3$OD] 2.03m (4H), 3.47m (5H), 4.08t (1H, J=10Hz), 6.88d (2H, J=8Hz), 7.62d (2H, J=8Hz) | — |
| 16 | B(CH$_3$CN) | CH$_3$COCH$_3$/(CH$_3$CH$_2$)$_2$O | 139-141 | [d$_6$-DMSO] 1.37-1.77m (6H), 3.03-3.63m (5H), 3.77s (3H), 4.07t (1H, J=10Hz), 5.13t (1H, J=10Hz), 7.00d (2H, J=8Hz), 7.37d (2H, J=8Hz) | — |
| 17 | B(CH$_3$CN) | CH$_3$COCH$_3$/(CH$_3$CH$_2$)$_2$O | 156 | [D$_2$O] 3.40-4.10m (10H), 3.83s (3H), 5.15dd (1H, J=8Hz, 10Hz), 7.00d (2H, J=8Hz), 7.37d (2H, J=8Hz) | — |
| 18 | B(CH$_3$OH/H$_2$O) | CH$_3$OH/(CH$_3$CH$_2$)$_2$O | 148-149 | [CD$_3$OD] 2.30s (3H), 3.07s (6H), 3.50d (1H, J=10Hz), 4.13t (1H, J=10Hz), 5.17dd (1H, J=8Hz, 10Hz), 7.07-7.43m (4H) | — |
| 19 | B(CH$_3$OH/H$_2$O) | CH$_3$OH/(CH$_3$CH$_2$)$_2$O | 152-153 | [CD$_3$OD] 2.30 (3H), 3.07s (6H), 3.50d (1H, J=8Hz, 10Hz), 4.13t (1H, J=10Hz), 5.17dd (1H, J=8Hz, 10Hz), 7.07-7.43m (4H) | -26.15 |
| 20 | B(CH$_3$CN) | CH$_3$OH/(CH$_3$CH$_2$)$_2$O | 156-158 | [CD$_3$OD] 2.97t (1H, J=2Hz), 3.17t (1H, J=10Hz), 3.53dd (1H, J=8Hz, 10Hz), 3.77s (3H), 4.27d (2H, J=2Hz), 5.20dd (1H, J=8Hz, 10Hz), 6.90d (2H, J=8Hz), 7.37d (2H, J=8Hz) | — |

TABLE I-continued

| Compound | Preparation (Reaction Solvent) | Crystallization Solvent | MP (°C.) | H NMR (δ) | $[\alpha]_D$ |
|---|---|---|---|---|---|
| 21 | B(CH₃OH/H₂O) | CH₃OH/(CH₃CH₂)₂O | 185-186 | [CD₃OD] 3.17s (6H), 3.53dd (1H, J=8Hz, 10Hz), 4.17t (1H, J=10Hz), 5.33dd (1H, J=8Hz, 10Hz), 7.40s (4H) | — |
| 22 | B(CH₃OH/H₂O) | CH₃OH/(CH₃CH₂)₂O | 187-189 | [CD₃OD] 3.03s (6H), 3.40dd (1H, J=8Hz, 10Hz), 4.08t (1H, J=10Hz), 5.13dd (1H, J=8Hz, 10Hz), 7.23-7.64m (3H) | — |
| 23 | B(CH₃OH/H₂O) | CH₃OH/(CH₃CH₂)₂O | 132-133 | [CD₃OD] 3.13s (6H), 3.52dd (1H, J=8Hz, 10Hz), 3.80s (3H), 4.17t (1H, J=10Hz), 5.20dd (1H, J=8Hz, 10Hz), 6.80-7.50m (4H) | — |

BIOLOGICAL ACTIVITY

The compounds of the present invention have antiarrhythmic activity and are useful in the suppression of various types of arrhythmias and in the prevention of the recurrence of tachyarrhythmias. They have been found to have effective antiarrhythmic activity while having minimal sympathomimetic effects and can be used in treating patients having cardiac arrhythmias.

The antiarrhythmic activity of these compounds was established by various procedures as described. While virtually all the compounds of the invention increased ventricular fibrillation threshold, the primary and secondary 2-aminoimidazolines were found to have pronounced sympathomimetic effects. Of the tertiary 2-aminoimidazolines, compound 6 (Table II) was found to have the best profile, consequently, the optical isomers were prepared and investigated. These additional studies showed that the l-isomer (compound 8) lacks the sympathomimetic activity of the racemic mixture and of the d-isomer (compound 7). Compound 6 is also active in the atrial flutter model although it is inactive in the ouabain induced arrhythmia model. These biological results have been summarized in Table II and compared to values for bretylium tosylate, the only currently marketed drug for treatment of ventricular fibrillation, and the experimental, orally active drug, bethanidine.

To determine the ventricular fibrillation threshold in the dog, the method of Joseph F. Spear; Moore, E. N.; and Gerstenblith described in *Circulation*, Volume XLVI, July 1972, pages 65–73, was followed. In this method a dog is anesthetized and the femoral artery and vein are cannulated. Pacing electrodes are then attached to the right atrial appendage. To determine ventricular fibrillation threshold (VFT) time, blood gases, esophageal temperature, and mean aterial pressure just prior to VFT determination are recorded. The treatment is also recorded. The stimulus is then applied and once fibrillation occurs, it is allowed to continue for fifteen seconds to determine if defibrillation occurs spontaneously.

TABLE II

| Compound | X | $R_1$ | $R_2$ | Y | ΔVFT | PHARMACOLOGY[1] ΔHR[2] (bpm) | ΔMAP[2] (mmHg) |
|---|---|---|---|---|---|---|---|
| 1 | 3,4-diCl | H | H | —NHCH$_3$ | + | | +++ |
| 2 | 4-CH$_3$O | H | H | —NH$_2$ | + | | +++ |
| 3 | 3-CH$_3$O | H | Bn | —NH$_2$ | + | | +++ |
| 4 | 3,4-diCl | H | H | —NH$_2$ | + | | +++ |
| 5 | 3-CH$_3$O | H | H | —NH$_2$ | + | | +++ |
| 6 | 4-CH$_3$O | H | H | —N(CH$_3$)$_2$ | + | −68 | −15(+45)[3] |
| 7 | 4-CH$_3$O | H | H | —N(CH$_3$)$_2$ | + | −22 | −13(+100)[3] |
| 8 | 4-CH$_3$O | H | H | —N(CH$_3$)$_2$ | + | −42 | +4(+15)[3] |
| 9 | 4-CH$_3$O | H | CH$_3$ | —NH$_2$ | + | | +++ |
| 10 | 4-CH$_3$O | H | CH$_3$ | —NHCH$_3$ | + | +41 | +58 |
| 11 | 4-CH$_3$O | H | CH$_3$ | —N(CH$_3$)$_2$ | + | −13 | −1 |
| 12 | 3-CH$_3$O | H | CH$_3$ | —NH$_2$ | + | | +++ |
| 13 | 3-CH$_3$O | H | CH$_3$ | —NHCH$_3$ | + | +69 | +70 |
| 14 | 3,4-diCH$_3$O | H | H | —N(CH$_3$)$_2$ | + | −24 | −7 |
| 15 | 4-CH$_3$O | H | H | —N(pyrrolidinyl) | + | −26 | −2 |
| 16 | 4-CH$_3$O | H | H | —N(piperidinyl) | ± | −48 | −30 |
| 17 | 4-CH$_3$O | H | H | —N(morpholinyl) | + | −36 | −21 |
| 18 | 4-CH$_3$ | H | H | —N(CH$_3$)$_2$ | + | −42 | −2 |
| 19 | 4-CH$_3$ | H | H | —N(CH$_3$)$_2$ | + | −37 | −10 |
| 20 | 4-CH$_3$O | H | H | —N(CH$_3$)CH$_2$C≡CH | + | −55 | −10 |
| 21 | H | H | H | —N(CH$_3$)$_2$ | + | +55 | +58 |
| 22 | 3,4-diCl | H | H | —N(CH$_3$)$_2$ | + | | +++ |
| 23 | 3-CH$_3$O | H | H | —N(CH$_3$)$_2$ | + | −40 | +53 |
| 24 | Bretylium | | | | + | +31 | +82(+42)[3] |

TABLE II-continued

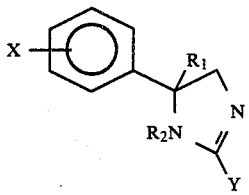

| Compound | X | $R_1$ | $R_2$ | Y | PHARMACOLOGY[1] | | |
|---|---|---|---|---|---|---|---|
| | | | | | $\Delta$VFT | $\Delta HR^2$ (bpm) | $\Delta MAP^2$ (mmHg) |
| 25 | Bethanidine | | | | + | +112 | +72(+27)[3] |

[1]$\Delta$VFT = change in ventricular fibrillation threshold,
$\Delta$HR = change in heart rate,
$\Delta$MAP = change in mean arterial pressure,
+ = increase,
− = decrease,
± = no change.
[2]Relative trends from $\Delta$VFT model; numerical values from P.B.-anesthetized, vagotomized dogs with data at 10 min.
[3]Data in parentheses taken at 30 min.

Defibrillation is then accomplished with the application of 10 to 20 joules extrapericardially. The results are tabulated in Table II.

The evaluation of chronotropic effects of compounds of the invention is determined in anesthetized, vagotomized, closed-chest dogs. A dog is anesthetized and an endotracheal tube is inserted. A cannula is inserted into the femoral vein for the administration of the compounds. The heart rate is recorded and the vagus nerve is vagotomized. The compound is injected by rapid I.V. bolus to determine the effect on heart rate. The peak change in mean arterial pressure is recorded. Doses are administered at 2 minute intervals. Control values, peak responses and time after dosing of peak responses are recorded. The change in heart rate is recorded in Table II.

What is claimed is:

1. A compound of the formula:

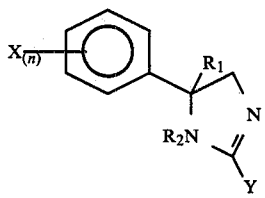

wherein Y denotes dimethylamino, methylpropynylamino, or pyrrolidino; $R_1$ denotes hydrogen or loweralkyl; $R_2$ denotes hydrogen or loweralkyl; X is loweralkyl, loweralkoxy, or halo; and n is an integer from 1 to 3 inclusive or a pharmaceutically acceptable salt thereof.

2. A compound of claim 1 wherein Y denotes dimethylamino or methylpropynyl-amino;
$R_1$ is hydrogen or loweralkyl;
$R_2$ is hydrogen;
X is loweralkyl, loweralkoxy, or halo; and
n is 1 or 2.

3. A compound of claim 2 wherein
Y is dimethylamino or methylpropynylamino;
$R_1$ is hydrogen or methyl;
$R_2$ is hydrogen;
X is methyl, methoxy, or chloro; and
n is 1 or 2.

4. A compound of claim 3 wherein
Y is dimethylamino or methylpropynylamino;
$R_1$ is hydrogen;
$R_2$ is hydrogen;
X is methoxy; and
n is 1 or 2.

5. The compound of claim 4 wherein
Y is dimethylamino;
$R_1$ and $R_2$ are each hydrogen;
X is methoxy; and
n is 1.

6. The compound of claim 5 where X is 4-methoxy.

7. The compound of claim 6 which is the l-isomer.

8. A method of treating or relieving cardiac arrhythmias in a patient comprising administering to a patient in need of such treatment a therapeutically effective amount of a compound of the formula:

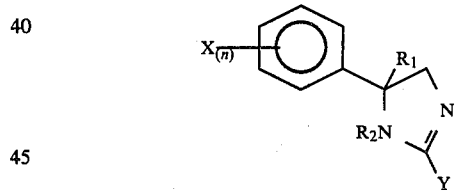

wherein Y denotes dimethylamino, methylpropynylamino, and pyrrolidino; $R_1$ denotes hydrogen or loweralkyl; $R_2$ denotes hydrogen or loweralkyl; X is loweralkyl, loweralkoxy, or halo; and n is an integer from 1 to 3 inclusive, or a pharmaceutically acceptable salt thereof.

9. The method of claim 8 wherein Y denotes dimethylamino or methylpropynyl-amino;
$R_1$ is hydrogen or loweralkyl;
$R_2$ is hydrogen;
X is loweralkyl, loweralkoxy, or halo; and
n is 1 or 2.

10. The method of claim 9 wherein Y is dimethylamino or methylpropynylamino;
$R_1$ is hydrogen or loweralkyl;
$R_2$ is hydrogen;
X is methyl, methoxy, or chloro; and
n is 1 or 2.

11. The method of claim 10 wherein Y is dimethylamino or methylpropynylamino;
$R_1$ is hydrogen;

R₂ is hydrogen;
X is methoxy; and
n is 1 or 2.

12. The method of claim 11 wherein Y is dimethylamino;
R₁ and R₂ are each hydrogen;
X is methoxy; and
n is 1.

13. The method of claim 12 wherein X is 4-methoxy.

14. The method of claim 13 wherein the compound is the l-isomer.

15. A pharmaceutical composition useful for the treatment of cardiac arrhythmia, which composition comprises an anti-arrhythmic effective amount of a compound the formula:

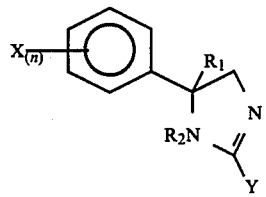

wherein Y denotes dimethylamino, methylpropynylamino, and pyrrolidino; R₁ denotes hydrogen or loweralkyl; R₂ denotes hydrogen or loweralkyl; X is loweralkyl, loweralkoxy, or halo; and n is an integer 1 to 3 inclusive, or a pharmaceutically acceptable salt thereof in admixture with a pharmaceutically acceptable carrier.

16. The composition of claim 15 wherein Y denotes dimethylamino or methylpropynylamino;
R₁ is hydrogen or loweralkyl;
R₂ is hydrogen;
X is loweralkyl, loweralkoxy, or halo;
n is 1 or 2.

17. The composition of claim 16 wherein
Y is dimethylamino or methylpropynylamino;
R₁ is hydrogen or methyl;
R₂ is hydrogen;
X is methyl, methoxy, or chloro;
n is 1 or 2.

18. The composition of claim 17 wherein
Y is dimethylamino or methylpropynylamino;
R₁ is hydrogen;
R₂ is hydrogen;
X is methoxy;
n is 1 or 2.

19. The composition of claim 18 wherein
Y is dimethylamino;
R₁ and R₂ are each hydrogen;
X is methoxy; and
n is 1.

20. The composition of claim 19 wherein X is 4-methoxy.

21. The composition of claim 20 which is the l-isomer.

* * * * *